(12) United States Patent
Gilbert et al.

(10) Patent No.: US 7,258,839 B2
(45) Date of Patent: Aug. 21, 2007

(54) TEMPERATURE CONTROLLED MICROFABRICATED TWO-PIN LIQUID SAMPLE DISPENSING SYSTEM

(75) Inventors: John Gilbert, Brookline, MA (US); Sebastian Böhm, Inverness (GB)

(73) Assignee: Cytonome, Inc., Watertown, MA (US)

( * ) Notice: Subject to any disclaimer, the term of this patent is extended or adjusted under 35 U.S.C. 154(b) by 389 days.

(21) Appl. No.: 10/328,973

(22) Filed: Dec. 23, 2002

(65) Prior Publication Data
US 2003/0194353 A1    Oct. 16, 2003

Related U.S. Application Data

(63) Continuation-in-part of application No. 10/027,171, filed on Dec. 21, 2001, now Pat. No. 7,041,257.

(60) Provisional application No. 60/372,562, filed on Apr. 11, 2002.

(51) Int. Cl.
*B01L 3/02* (2006.01)
*G01N 1/10* (2006.01)

(52) U.S. Cl. ............... 422/100; 422/105; 436/180; 73/863.11

(58) Field of Classification Search ........ 422/100, 422/105, 107–109; 436/180, 55; 73/863.11
See application file for complete search history.

(56) References Cited

U.S. PATENT DOCUMENTS

| | | | |
|---|---|---|---|
| 3,885,440 A | 5/1975 | Rossfelder | 73/425.2 |
| 4,116,069 A | 9/1978 | Lezgintsev et al. | 73/425.2 |
| 4,659,677 A | 4/1987 | Glover et al. | 436/174 |
| 5,028,988 A * | 7/1991 | Porter et al. | 257/716 |
| 5,096,676 A | 3/1992 | McPherson et al. | 117/206 |
| 5,260,030 A | 11/1993 | DeVaughn | 422/100 |
| 5,356,052 A | 10/1994 | Poynter | |
| 5,417,362 A * | 5/1995 | Chiyonobu et al. | 228/180.1 |
| 5,643,540 A | 7/1997 | Carter et al. | 422/245.1 |
| 5,741,554 A | 4/1998 | Tisone | 427/424 |
| 5,770,151 A | 6/1998 | Roach et al. | 422/63 |

(Continued)

FOREIGN PATENT DOCUMENTS

EP    1118582 A2    7/2001

(Continued)

OTHER PUBLICATIONS

Blanchard, A.P. et al. "High-density oligonucleotide arrays" *Biosensors & Bioelectronics* 11(6/7):687-690 (1996).

(Continued)

*Primary Examiner*—Brian R. Gordon
(74) *Attorney, Agent, or Firm*—Lahive & Cockfield LLP; Elizabeth A. Hanley; David R. Burns

(57) ABSTRACT

A cooled liquid sample dispensing system comprises a pair of pins for holding a droplet of liquid therebetween and a cooling element. Each pin includes a tip spaced predetermined distance from the other pin to define a sample acquisition region. The pins acquire and hold a droplet of the liquid sample in the sample acquisition region formed in the space between the tips and apply the droplet to a selected sample handing system. The cooling element, when activated, cools the droplet of liquid to reduce evaporation.

31 Claims, 8 Drawing Sheets

U.S. PATENT DOCUMENTS

| | | | |
|---|---|---|---|
| 5,807,522 A | 9/1998 | Brown et al. ................. 422/50 |
| 5,922,591 A * | 7/1999 | Anderson et al. ......... 435/287.2 |
| 5,957,167 A | 9/1999 | Feygin ........................ 141/31 |
| 5,962,329 A * | 10/1999 | Ershov et al. ................ 436/50 |
| 6,001,231 A | 12/1999 | Kopf-Sill .................... 204/454 |
| 6,024,925 A | 2/2000 | Little et al. .................. 422/100 |
| 6,039,804 A | 3/2000 | Kim et al. ................... 117/206 |
| 6,086,825 A | 7/2000 | Sundberg et al. ........... 422/100 |
| 6,101,946 A | 8/2000 | Martinsky ................... 101/494 |
| 6,110,426 A | 8/2000 | Shalon et al. .............. 422/68.1 |
| 6,163,339 A * | 12/2000 | Meunier ................... 348/218.1 |
| 6,174,365 B1 | 1/2001 | Sanjoh ........................ 117/68 |
| 6,245,297 B1 | 6/2001 | Kowallis ....................... 422/66 |
| 6,255,119 B1 | 7/2001 | Baier ......................... 436/180 |
| 6,258,331 B1 | 7/2001 | Sanjoh .................... 422/245.1 |
| 6,269,846 B1 | 8/2001 | Overbeck et al. ............. 141/1 |
| 6,296,702 B1 | 10/2001 | Bryning et al. ............. 118/401 |
| 6,303,387 B1 | 10/2001 | Birch et al. ................. 436/180 |
| 6,309,891 B1 | 10/2001 | Shalon et al. .............. 436/180 |
| 6,328,483 B1 * | 12/2001 | Havasi et al. ................ 385/92 |
| 6,365,349 B1 | 4/2002 | Moynihan et al. ............. 435/6 |
| 6,387,330 B1 | 5/2002 | Bova et al. .................. 422/100 |
| 6,413,586 B2 | 7/2002 | Vann et al. .................. 427/256 |
| 6,566,520 B2 * | 5/2003 | DeWitt et al. .............. 544/363 |
| 6,640,891 B1 * | 11/2003 | Oldenburg .................. 165/253 |
| 6,663,294 B2 * | 12/2003 | Crane et al. .................. 385/92 |
| 6,692,972 B1 * | 2/2004 | Yershov et al. ............. 436/180 |
| 6,712,528 B2 * | 3/2004 | Galeotti et al. ............... 385/91 |
| 2001/0005545 A1 | 6/2001 | Andou et al. ............... 428/209 |
| 2001/0049149 A1 | 12/2001 | Kennedy et al. ............ 436/180 |
| 2005/0138934 A1 * | 6/2005 | Weigert et al. ............... 62/3.2 |

FOREIGN PATENT DOCUMENTS

| | | |
|---|---|---|
| EP | 1118582 A3 | 7/2001 |
| WO | WO 02/073159 A2 | 9/2002 |
| WO | WO 02/073159 A3 | 9/2002 |
| WO | WO 03/000422 A1 | 1/2003 |

OTHER PUBLICATIONS

Lemieux, B. et al. "Overview of DNA chip technology" *Molecular Breeding* 4:277-289 (1998).

Schena, M. et al. "Microarrays: biotechnology's discovery platform for functional genomics" *Trends in Biotechnology* 16(7):301-306 (Jul. 1998).

Shalon, D. et al. "A DNA Microarray System for Analyzing Complex DNA Samples Using Two-color Fluorescent Probe Hybridization" *Genome Research* 6(7):639-645 (Jul. 1996).

* cited by examiner

TEMPERATURE CONTROLLED MICROFABRICATED TWO-PIN LIQUID SAMPLE DISPENSING SYSTEM

RELATED APPLICATIONS

The present application claims priority to U.S. Provisional Patent Application Ser. No. 60/372,562, filed Apr. 11, 2002, and is a continuation-in-part patent application of U.S. patent application Ser. No. 10/027,171, filed Dec. 21, 2001, now U.S. Pat. No. 7,041,257 the contents of which are expressly incorporated herein by reference.

FIELD OF THE INVENTION

The present invention relates to a liquid dispensing system having reduced evaporation for forming and dispensing droplets of a liquid sample and a method for reducing evaporation in a liquid dispensing system

BACKGROUND OF THE INVENTION

Many chemical, biomedical, bioscience and pharmaceutical industries require chemical operations, such as reactions, separations and subsequent detection steps, to be performed on samples. It is generally desirable to introduce these samples into a sample handling system, such as a microfluidic system capable of handling and analyzing chemical and biological specimens, quickly, efficiently and in a highly controllable manner.

Many known methods have been described for interfacing a fluid, e.g., a biological, biochemical or chemical sample, analyte, reagent, precursor for synthesis, and buffer, towards, within or between microfluidic systems. Generally, introduction of a liquid sample to a microfluidic system is accomplished through sample channels or sample wells. To introduce a liquid sample to the microfluidic system, a capillary tube may be provided, which dispenses a liquid sample to a sample well, sample channel or other sample introduction port. A significant drawback of using a capillary tube concerns the low injection efficiency inherent to capillary tubes, that is, the ratio between the volume of liquid required for a particular chemical operation in a part of the microfluidic system, and the total volume of liquid required for the introductory operation. Moreover, it is generally difficult to control the precise volume of dispensed sample using capillary tubes. Furthermore, capillary tubes are subject to contamination, because the same port used to fill the tube is also used to eject the liquid sample.

U.S. Pat. No. 6,101,946 of Martinsky, the contents of which are herein incorporated by reference, describes a pin-based system for printing microarrays of biochemical substances. The microarray printing system comprises a stainless steel printing pin having a sample channel and a flat tip that is machined with an electronic discharge machine (EDM). The pin applies a biochemical substance by filling the sample channel and subsequently directly contacting a printing substrate, to deliver the sample from the sample channel to the printing substrate. A drawback of the pin-based system described in the '946 patent concerns the ability to control the amount of delivered sample. The pin-based system is subject to contamination and breakage, because it requires direct contact between the pin tip and the printing substrate. Another drawback concerns the difficulty of precisely positioning the tip of the pin to provide sufficient contact to result in delivery of a sample.

U.S. Pat. No. 6,110,426 of Shalon et al., the contents of which are herein incorporated by reference, describes a capillary dispenser for forming microarrays of biological samples. The capillary dispenser comprises an elongate open capillary channel adapted to hold a liquid sample. The channel is formed by a pair of spaced-apart, coextensive, elongate members, which are tapered toward one another and converge at a tip region at the lower end of the channel. The elongate members are fixed relative to each other and the capillary channel is limited to a fixed volume. Furthermore, it is difficult to control the amount of sample that is acquired and dispensed from the capillary dispenser of the '246 patent.

Using these types of devices, a large number of spots of the same liquid can be produced. However, during operation, the liquid sample potentially evaporates from the device, which is disadvantageous for many applications. Evaporation of the sample gives rise to a number of unwanted phenomena, such as increasing concentration of substances in the liquid to be spotted, crystallization and denaturation of substances in the liquid.

SUMMARY OF THE INVENTION

The present invention provides for a fluid handling system comprising one or more microfabricated pin assemblies for handling fluid droplets. The fluid handling system reduces evaporation of a fluid by incorporating a temperature control element, such as a cooling element, for controlling the temperature (e.g., cool) the fluid handled by the fluid handling system. The pin assembly preferably includes two or more pins, each of which includes a tip spaced predetermined distance from the other tip to define a fluid acquisition region. The pins handle (e.g., acquire and hold) a droplet of the fluid in the fluid acquisition region formed in the space between the tips. The temperature of the droplet is controlled by the integrated temperature control element to prevent or reduce evaporation of the fluid.

According to one aspect, a temperature control system is also included in the fluid handling system for controlling the temperature of the fluid.

DETAILED DESCRIPTION OF THE ILLUSTRATIVE EMBODIMENTS

The present invention provides a fluid handling system for handling a predetermined volume of liquid sample. As used herein, the term "handling" is intended to include manipulating, retrieving, dispensing, acquiring or delivering a fluid, or any means for conveying the fluid. The system of the present invention provides for precision handling of a fluid, such as acquisition and delivery of a liquid sample to fluid sample handling system using one or more pin assemblies having at least two interacting pins. The invention will be described below relative to an illustrative embodiment. Those skilled in the art will appreciate that the present invention may be implemented in a number of different applications and embodiments and is not specifically limited in its application to the particular embodiment depicted herein. Those of ordinary skill will readily recognize that the pin assembly can include one of more pins, and any number of additional electrical, mechanical, electro-mechanical, magnetic or hybrid-type components or parts, including but not limited to one or more of an actuator, temperature control element, sensor, circuitry, controller, support elements, holder and the like. The pin assembly can employ one or more pins having any selected shape, configuration and arrangement. Likewise, the fluid handling system of the invention can include one or more pin assemblies, and if desired any number of additional components, such as any number of additional electrical, mechanical, electromechanical, magnetic or hybrid-type components or parts, including but not limited to one or more conventional pin assembly handling or moving systems, support assemblies, temperature control elements, sensors, circuitry, controllers, holders and the like.

Figure 1A:
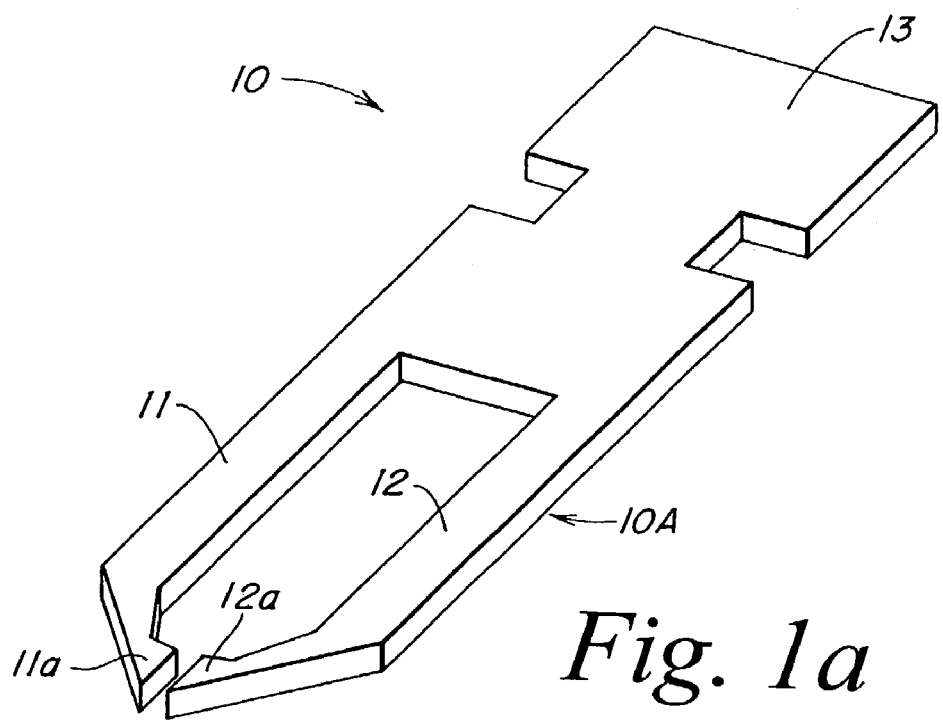
FIG. 1a illustrates a microfabricated fluid handling system employing a pin assembly according to the teachings of the present invention.
Figure 1B:
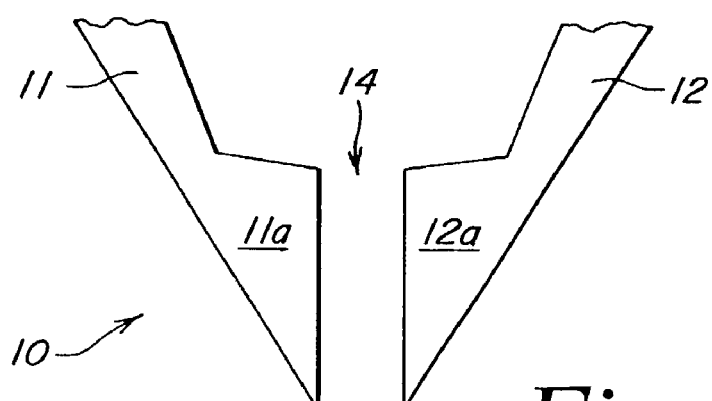
FIG. 1b illustrates a tip region of the fluid handling system of FIG. 1a, which according to one embodiment is fabricated to hold about 1.2 nanoliters of liquid.

FIGS. 1a and 1b illustrate a microfabricated fluid handling system 10 according to the teachings of the present invention. The fluid handling system 10 includes a pin assembly, generically designated as assembly 10A, that includes at least a pair of pins sized and configured to hold a droplet of fluid between the tips of the pins. Specifically, the pin assembly comprises a first pin 11 and a second pin 12, which are connected to a holder 13. The pin tips 11a and 12a are separated by an initial separation distance D (FIG. 2a) to form a fluid or sample acquisition region 14 in the space between the tips. For purposes of simplicity, we will describe the fluid handling system of the invention as handling a liquid sample.

To acquire a droplet of a liquid sample, the pin tips 11a and 12a are immersed in a reservoir containing a supply of a selected liquid sample. The pin tips 11a and 12a are positioned to allow capillary flow into a sample acquisition region 14 formed between the tips. The capillary force induced in the sample acquisition region 14 pulls or draws a droplet therebetween having a volume defined by the separation distance D and the shape of the pin tips 11a and 11b. The capillary force produced between the surfaces of the pin tips holds the droplet in the sample acquisition region 14. As shown in FIG. 1b, the fluid handling system 10 may be used to hold a droplet having a volume of between about 0.1 nanoliters and about 50 nanoliters. FIG. 1b illustrates a system holding a 1.2 nanoliter volume of liquid in the sample acquisition region between the tips 11a, 11b, though one skilled in the art will recognize that the invention is not limited to the described volume. Specifically, the pin assembly can be designed so as to handle any desired liquid volume. Those of ordinary skill will readily recognize that either one of the pins 11 and 12 can be constructed so as to be rigid or non-movable, flexible, or movable, or designed to include or to impart any desired functionality.

Figure 2A:
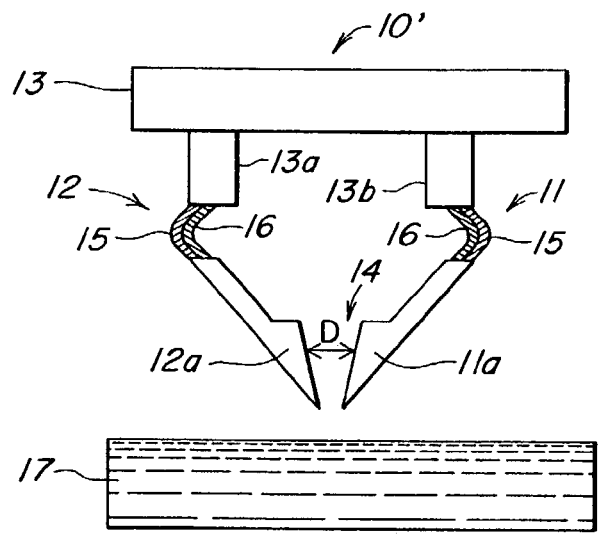
FIGS. 2a and 2b illustrate the operation of the fluid handling system in a sample acquisition mode according to the teachings of the present invention.
Figure 2B:
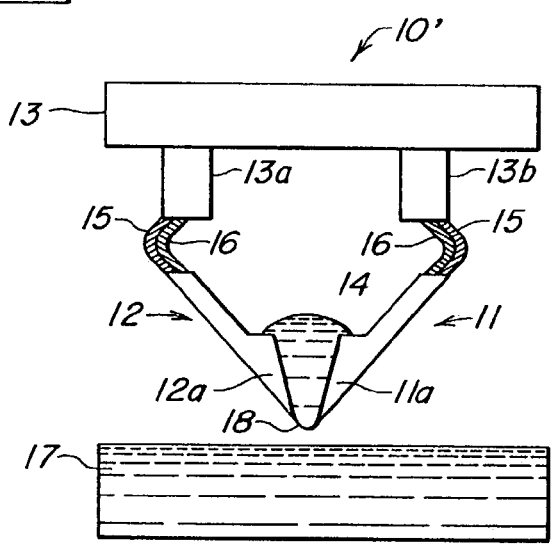

FIGS. 2a and 2b illustrate another embodiment of the fluid handling system according to the teachings of the present invention. The illustrated fluid handling system 10' is illustrated in a sample acquisition mode for acquiring a droplet of a liquid sample having a predetermined volume from a reservoir containing a supply of the liquid sample. Like parts are designated with the same reference numerals. The fluid handling system 10' of FIGS. 2a and 2b comprises a pair of separately movable interacting pins sized and configured to hold a droplet of liquid between the tips of the pins. Similar to the fluid handling system 10 of FIG. 1, the fluid handling system 10' comprises a first pin 11 and a second pin 12, which are separated by an initial separation distance D to form a sample acquisition region 14 in the space between the tips. The tips 11a and 12a may be movably coupled or connected to a holder 13. The position of each pin is controlled using actuators 15 located in one or more of the pins 11 and 12. According to an alternate embodiment, one or more sensors 16 can be optionally provided on one or more of the pins 11 and 12 to sense movement of the pin. The sensor can generate an output signal that can be received and used by associated circuitry or a controller for determining or measuring the separation distance D between the pin tips 11a, 12a. Those of ordinary skill in the art will readily recognize that the holder of the invention can include any suitable structure for supporting, retaining, affixing, securing or holding the pins. The illustrated holder 13 can include one or more support stanchions 13a for coupling to the pin assembly.

To acquire a droplet of a liquid sample, the pin tips 11a and 12a are immersed in a reservoir 17 containing a supply of a selected liquid sample. The pin tips 11a and 12a are positioned to allow capillary flow into the sample acquisition region 14. The capillary force induced in the sample acquisition region 14 pulls a droplet 18 having a volume defined by the separation distance of the pin tips 11a, 11b, into the sample acquisition region 14. The capillary force produced between the surfaces of the pin tips holds the droplet in the sample acquisition region 14 formed between the two pin tips 11a, 11b. The actuators 15 in the pins 11, 12 move the pins to vary the separation distance D between the tips, thereby varying the amount of sample that is acquired by the two-pin fluid handling system, or to handle the sample therefrom. The actuators 15 can be integrally formed with the pin, or can be coupled or connected between the pin and the holder.

According to one practice, the fluid handling system of the invention is configured to handle (e.g., acquire) liquid samples in volumes between about 0.1 nanoliters and about 50 nanoliters. One skilled in the art will recognize that the acquired volume is not limited to this range and that the pins may be spaced apart to accommodate any suitable volume of liquid.

The actuators 15 can also compensate for varying physical properties of the particular liquid sample, such as viscosity, surface tension, and the like, by modifying the separation distance D between the pins. The sensors 16 may also be utilized to measure the force applied between the tips and the physical properties of the acquired liquid sample on the fly. In this manner, the settings (i.e. the pin separation distance) of the fluid handling system 10' can be modified to compensate for variations in the measured properties of the liquid sample in real time.

According to the illustrative embodiment, the fluid handling systems 10 and 10' and/or pin assemblies 10A are fabricated from a silicon wafer using a microfabrication technique, such as a standard photolithography etching process, to fabricate the pin structures. One skilled in the art will recognize that alternative materials and manufacturing techniques may be utilized. For example, the fluid handling system and/or pin assembly 10A may be made out of glass, plastic or any other suitable material. According to one embodiment, an array of fluid handling systems 10, each comprising two pins forming a channel therebetween, may be formed on a single substrate, such as a silicon wafer. For example, an array of up to about 300 or more fluid handling systems 10 or pin assemblies may be formed on a four-inch silicon wafer.

Figure 3:
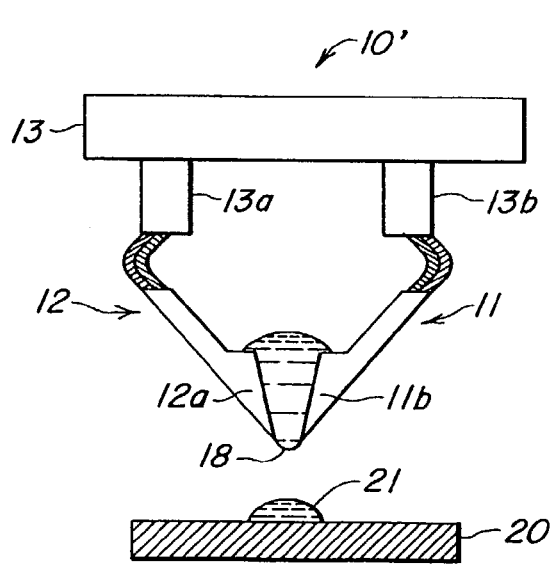
FIG. 3 illustrates the fluid handling system of FIGS. 2a and 2b in a spotting mode according to the teachings of the present invention.

FIG. 3 illustrates the fluid handling system 10' of the invention disposed in a sample spotting mode. The fluid handling system 10' may be utilized as a spotting system for printing or discharging arrays of biochemicals, such as nucleic acid molecules or proteins, or other suitable liquid samples to a sample handing system, such as a printing substrate, titre plate, microfluidic system or device, and the like for use in proteomics, genomics, screening, diagnostics and other applications. After the fluid handling system acquires a droplet, the fluid handling system is moved in close proximity to a surface 20. The surface 20 may comprise a solid surface or a liquid. The surface 20 may comprise a porous structure, such as a porous membrane, or a non-porous structure, such as a microscope slide. The loaded pins deposit a spot 21 on the surface 20 having a selected spot volume by direct contact between the pin tips 11a, 11b and the surface. The separation distance D2 during contact may be varied to increase or decrease the volume of the dispensed spot of the liquid sample. According to the illustrative embodiment, the volume of the dispensed spot 21 is significantly smaller than the volume of the acquired droplet 18, and is generally sub-nanoliter in volume, though one skilled in the art will recognize that the invention is not limited to this range.

The use of the fluid handling system of the invention in spotting applications provides enhanced control over the size of the deposited spots in a microarray, and also allows for smaller spots to be formed and deposited.

Figure 4A:
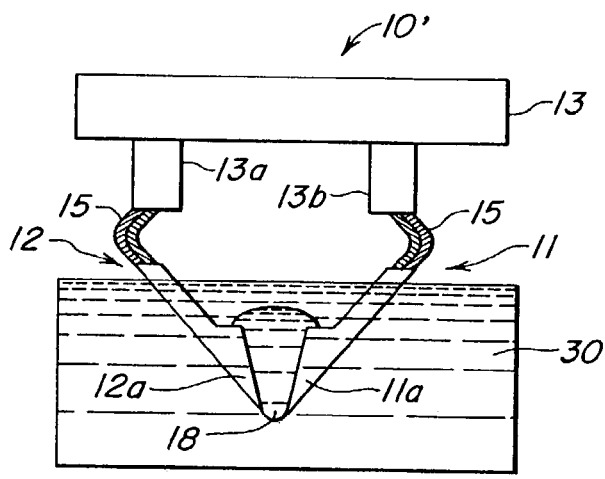
FIGS. 4a and 4b illustrate the fluid handling system of FIGS. 2a and 2b in a dilution mode according to the teachings of the present invention.
Figure 4B:

The fluid handling system may further be utilized as a wet deposit system to dilute a selected volume of a first liquid in a second liquid sample. FIGS. 4a and 4b illustrate the fluid handling system 10' in a dilution mode, wherein the acquired droplet 18 of a sample is diluted in a larger supply of a target fluid 30. After the fluid handling system 10' acquires a droplet 18, the size of which is defined by the separation distance of the pin tips 11a and 12a, the pin tips 11a, 12a are immersed in a reservoir 30 containing a target fluid. The droplet 18 automatically dilutes into the target fluid via mixing and diffusion. To accelerate the dilution process, the separation distance of the tips 11a, 12a may be increased during dilution using the actuators 15.

Figure 5:
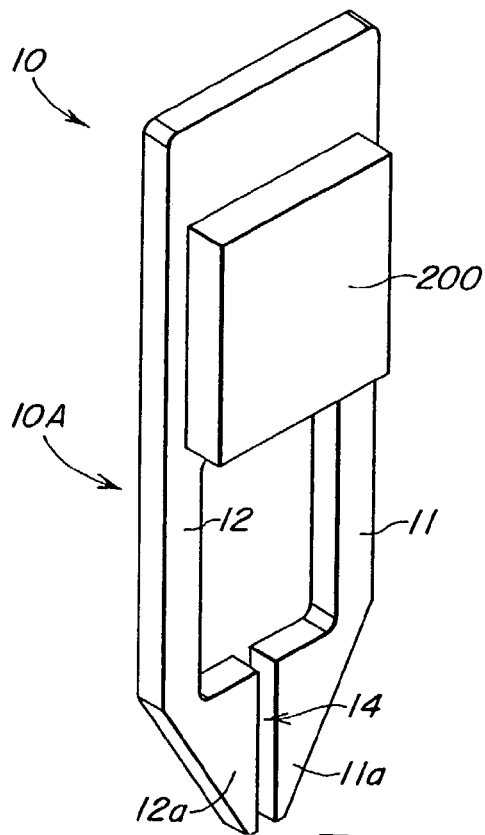
FIG. 5 illustrates another embodiment of the fluid handling system including a temperature control element according to the teachings of the present invention.

FIG. 5 illustrates another embodiment of the fluid handling system of the present invention. Like parts are designated with like reference numerals. The illustrated fluid handling system 10 includes a temperature control element 200 for controlling, varying or regulating the temperature of the liquid sample being handled. The temperature-controlled fluid handling system 10 comprises a first pin 11, a second pin 12 and a temperature control element 200 for controlling the temperature of the pin assembly and/or the liquid sample. For example, the temperature control element can heat or cool the pin assembly or the liquid sample. The temperature control element can be any device suitable for cooling or heating any component of the fluid handling system 10, and is preferably a thermoelectric module, such as a Peltier element. The temperature control element can form part of the fluid handling system 10, the pin assembly 10A, or can be provided as a separate independent component. The first pin 11 and the second pin 12 are positioned relative to each other to form a sample acquisition region, illustrated as a channel 14 formed between the two tip elements 11a and 12a defining the sample acquisition region. The temperature control element 200 is coupled, connected, affixed, secured or otherwise disposed in temperature communication with a surface on a base or sample-receiving substrate. Upon activation of the temperature control element 200, the temperature of the fluid handling system 10 is changed, to either promote or control evaporation of the sample.

One skilled in the art will recognize that any suitable means for controlling the temperature of the liquid carried by the pin of the fluid system may be utilized according to the teachings of the invention.

Figure 6:
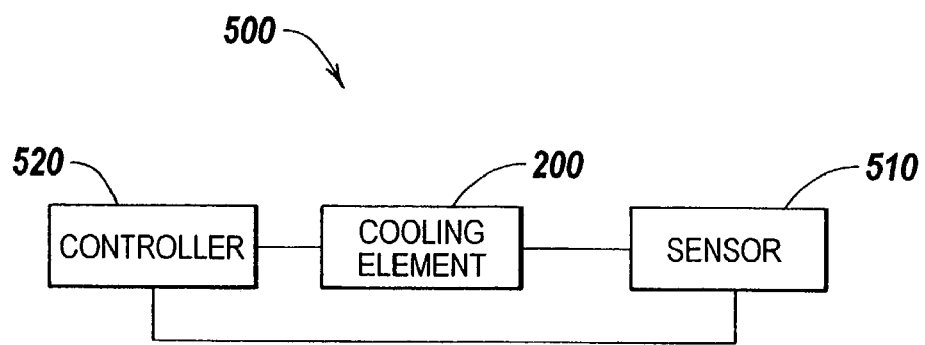
FIG. 6 is a schematic block diagram of a temperature control system suitable for operation with the fluid handling system of FIG. 5.

According to another embodiment of the invention, the temperature-controlled fluid handling system 10 may further include a temperature control circuit, shown in FIG. 6, for controlling the temperature of the system 10 or the liquid sample carried by the system. For example, the temperature-controlled fluid handling system 10 may include a temperature control system 500 for comparing an actual temperature of a component of the system, such as one of the pins or the liquid sample, to a reference temperature and adjusting the actual temperature to reduce any deviation between the actual temperature and the reference temperature. The temperature control system 500 includes a temperature sensor 510 for continuously measuring the temperature of the liquid sample or fluid system and a controller 520 for controlling the temperature control element 200 in response to the temperature detected by the sensor 510. The controller 520 compares the detected temperature to the set reference temperature. If the detected temperature deviates from the set reference temperature, the controller 520 triggers the cooling element 200 to increase or decrease cooling, in order to maintain the temperature of the system or liquid at the set reference temperature. Although illustrated as a feedback system, those of ordinary skill will readily recognize that the system 500 can also be configured as an open loop system.

The sensor 510 may comprise a thin film resistor, formed of conductive metals, carbon, a semi-conductor or any suitable material. The sensor is preferably integrated with the temperature-controlled two-pin fluid system and continuously measures the operating temperature of the system 10. One skilled in the art will recognize that any suitable temperature sensor and controller may be utilized in order to actively control the temperature of the two-pin fluid system.

FIGS. 7a-7h are detailed views of the tip region of the two pins 11, 12 of the fluid handling system, illustrating different shapes suitable for liquid sample handling. As shown, the sample acquisition region 14 may be spherical, cylindrical, conical, cubic or any other suitable shape.

Figure 7A:
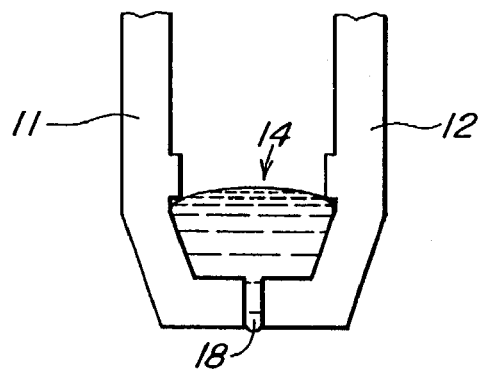
FIGS. 7a-7h are detailed views of the tip region of an exemplary pin assembly of the invention, illustrating different pin tip shapes.
Figure 7B:
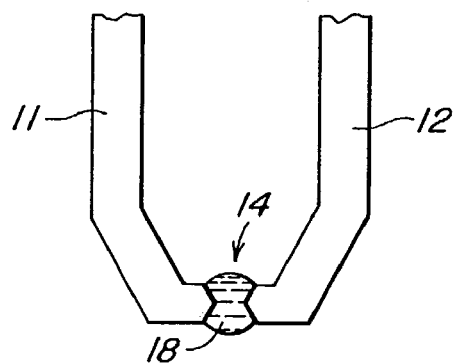

As shown in FIGS. 7a and 7b, the tip contact surfaces 70 defined by the tip heights H and tip depths S may form parallel faces or, according to another embodiment, may be tapered, so that the separation distance D is reduced towards the bottom and/or front of the tip surface. In this manner, smaller droplet volumes may be accommodated. The slope of the tips 11a, 12a may be varied in regions 71 and 72 to improve droplet shape and enhance delivery of the droplet.

Figure 7C:
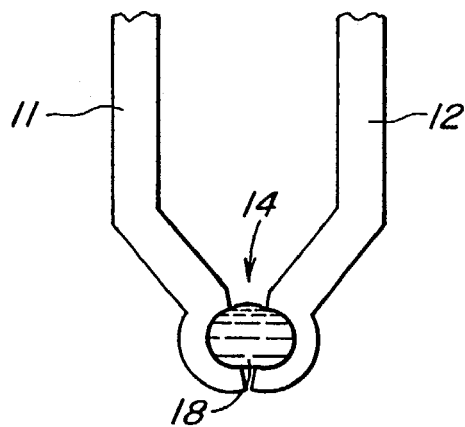
Figure 7D:
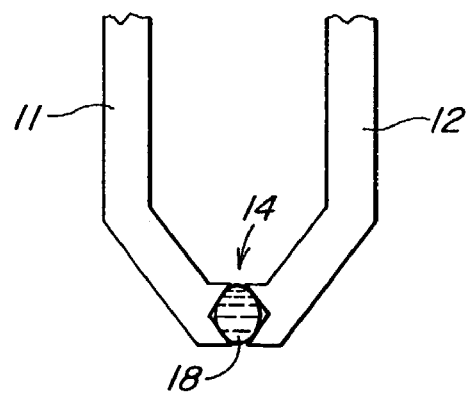
Figure 7E:
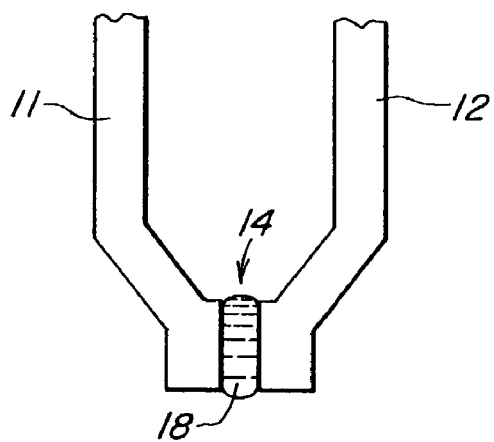
Figure 7F:
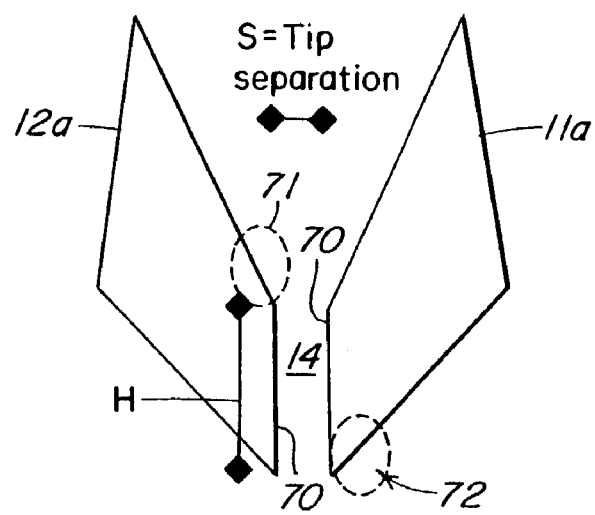
Figure 7G:
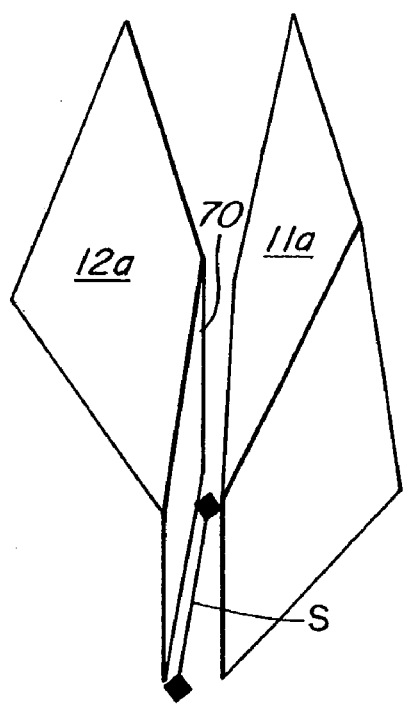
Figure 7H:
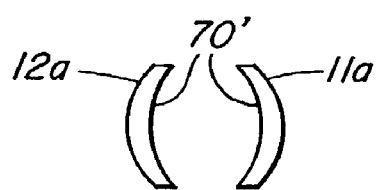

FIG. 7c is a cross-sectional view of the tips 11a, 12a according to an alternate embodiment. According to alternate embodiment, the tip surfaces 70' are curved to hold form a cylindrical or conical sample acquisition region 14 therebetween.

Figure 8:
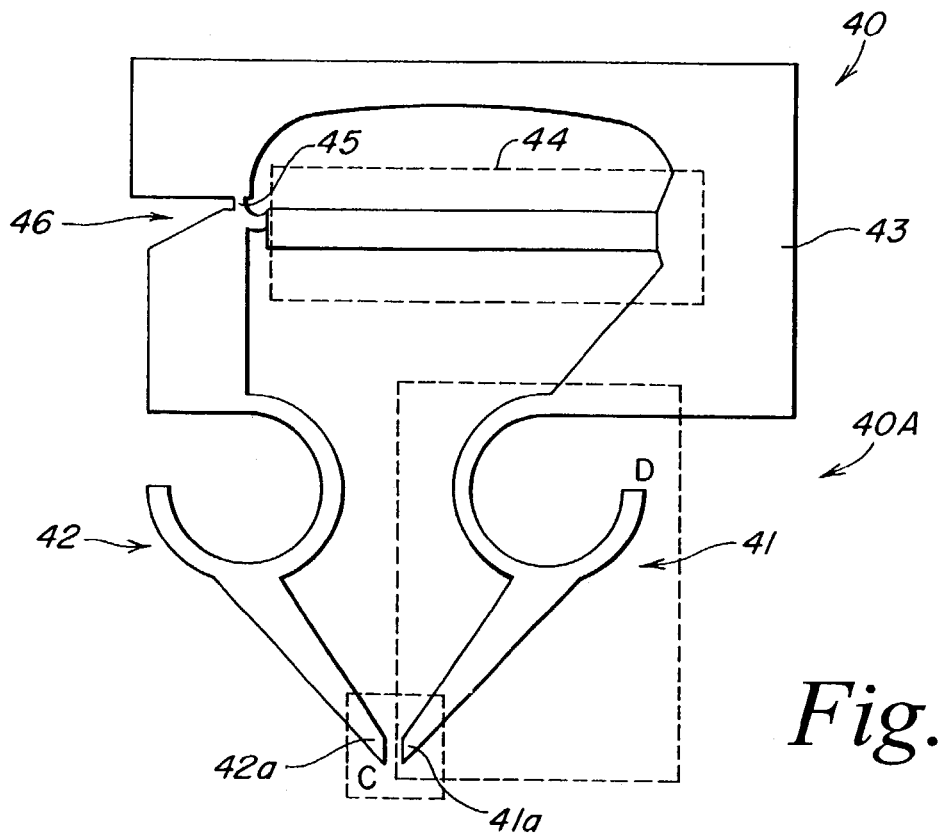
FIG. 8 is a schematic view of an alternate embodiment of the fluid handling system of the invention employing a fixed pin and a movable pin.

FIG. 8 illustrates another embodiment of the fluid handling system according to the teachings of the present invention. The illustrated fluid handling system 40 includes a pin assembly 40A having at least a fixed pin 41 and a movable pin 42. In the fluid handling system of FIG. 8, the resting position of a first pin 41 is fixed relative to a substrate 43 and the resting position of the second pin 42 is movable relative to the first pin 41 and the substrate 43. The fluid handling system 40 further includes a driver 44 for varying the separation distance between the tips 41a, 42a by adjusting or moving the position of the second movable pin 42 by acting upon the fulcrum region 46. According to the illustrated embodiment, the movable pin 42 rotates about a fixed pivot point 45 under the control of the driver 44 to adjust the separation distance at the tips.

The illustrated pins 41 and 42 can also include a relaxation region 51 for preventing breakage of the tips. One skilled in the art will recognize that the relaxation region 51 may be formed in one or both of the pins 41, 42 of the fluid handling system 40.

The illustrated fluid handling system 40 is formed from a silicon wafer using a standard photolithography etching process to fabricate the pins 41, 42, the relaxation region 51, the driver 44, and the fixed point 45 of the fulcrum region 46 in the wafer substrate 43. According to the illustrated embodiment, the fluid handling system 40 and/or pin assembly 40A is fabricated from a silicon wafer having dimensions of about one square centimeter. The pins 41,42 have a length of about five millimeters, though one skilled in the art will recognize that the invention is not limited to this size, and indeed can include any suitable or desired size. According to an alternate embodiment, a larger silicon wafer or other suitable substrate is provided, and an array of fluid handling systems is fabricated on the larger silicon wafer. For example, a silicon wafer having a size of about ten square centimeters may be used to fabricate an array of about seventy two-pin fluid handling systems 40 thereon. A fifteen square centimeter silicon wafer can be utilized to fabricate over one hundred two-pin fluid handling systems 40 in the silicon wafer substrate. Those of ordinary skill will readily recognize that any suitable configuration can be employed to move one or both of the pins.

Figure 9:
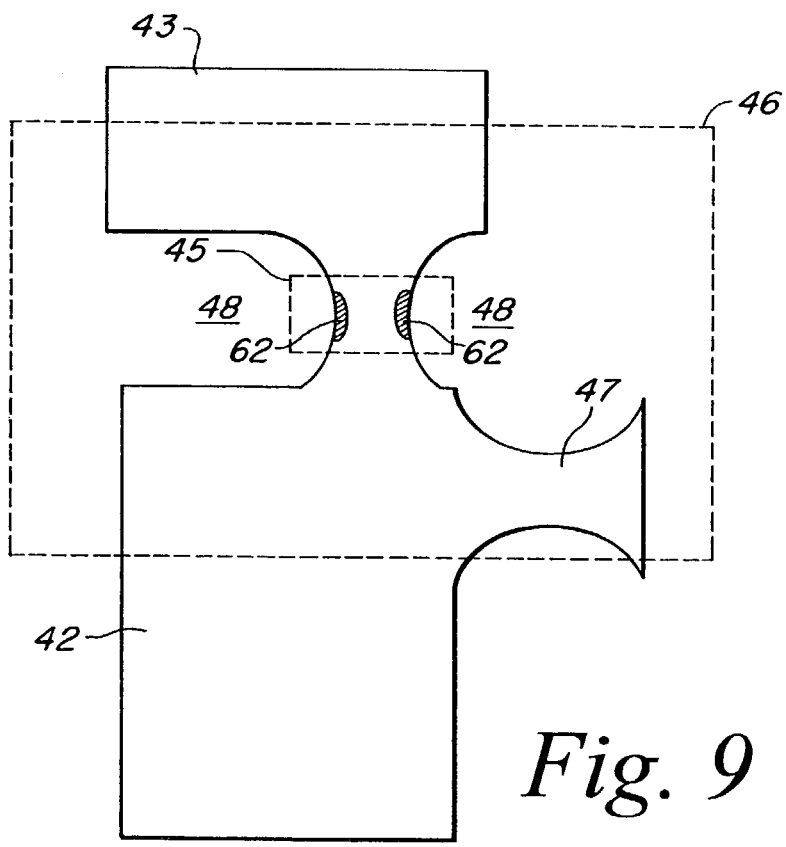
FIG. 9 is a detailed view of the fulcrum region of the fluid handling system of FIG. 8.

FIG. 9 is a detailed view of the fulcrum region 46 of the fluid handling system of FIG. 8. The movable pin 42 is configured to pivot about a fixed point 45 to vary the separation distance of the two pin tips. The driver 44 applies a force to an application region 47 of the fulcrum region 46 to cause the movable pin 42 to rotate, thereby effecting movement of the movable pin tip 42a relative to the tip 41a of the fixed pin 41. As illustrated, the fulcrum region 46 includes gaps 48 are formed in the substrate 43 adjacent to the fixed point 45 to allow for rotation of the pin 42 about the fixed point in response to activation of the driver 44.

According to an alternate embodiment of the invention, the fulcrum region can optionally include one or more bending sensors, illustrated as piezoresistors 62, on the left and right side of the fulcrum region to allow differential sensing of actual bending of the pin 42 in the fulcrum region. In this manner, the amount of bending, and the resultant tip separation distance may be controlled using a closed loop feedback system. The use of bending sensors further limits nonlinear temperature effects by allowing real-time sensing of tip displacement.

Figure 10:
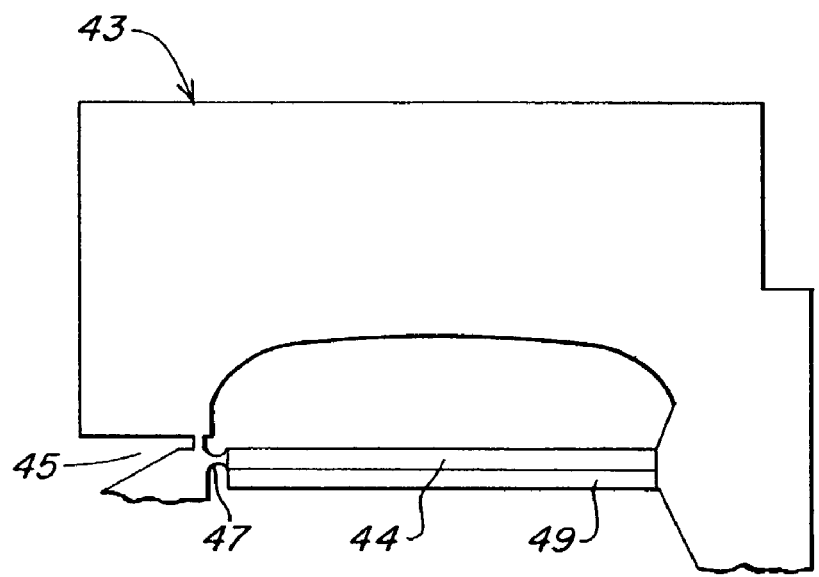
FIG. 10 is a detailed view of the driver of the fluid handling system of FIG. 8.

FIG. 10 is a detailed view of the driver 44 of the fluid handling system 40 of FIG. 8. The illustrated driver can comprise any suitable component or assembly that is capable of applying a selected force. According to one embodiment, for example, the illustrated driver 44 comprises a bar of silicon that imparts a force on the application region 47 of the fulcrum 46 to move of tip 42a a predetermined amount. According to the illustrative embodiment, the driver 44 expands a predetermined amount in response to a temperature increase. The expansion of the driver 44 forces rotation of the fulcrum about the pivot point.

According to one practice, the illustrated system is configured such that the ratio between the amount of movement of the tip 42a in response to expansion of the driver 44 to the amount of expansion of the driver is greater than one hundred. Specifically, a driver expansion of one micron causes a one hundred micron displacement of the pin tip 42a.

According to the illustrative embodiment, the driver 44 has an initial length L of four millimeters. A thirty-degree rise in temperature of the silicon results in a 1.08 micrometer expansion of the driver 44. The expansion of the driver 44 forces the pin 42 to rotate about the fixed pivot point 45, thereby increasing the separation distance between the tips 41a, 42a by greater than 108 microns.

According to the illustrative embodiment, a temperature control element can be coupled or affixed to the driver 44. For example, a heating element, such as a heating resistor 49, can be optionally coupled or affixed to the driver for applying heat thereto. The heating resistors may comprise poly resistors, diffused resistors or any suitable means for applying heat to the driver 44 in order to effect controlled expansion of the driver 44 and to vary the separation distance between the tips 41a, 42a. Optionally, cooling fins (not shown) are provided in the driver 44 near the fulcrum region 45 to prevent unwanted heating of the driver in the fulcrum region. According to an alternate embodiment, a temperature sensor (not shown) in communication with the heating means is included in the two-pin fluid handling system 40 to provide closed loop control of the driver 44 temperature.

One skilled in the art will recognize that the fluid handling system is not limited to the illustrative driver. According to alternate embodiments, the driver 44 comprises an electrostatic system, a piezoelectric system, an electromechanical system, a thermoelectric actuator or any suitable system for applying a predetermined and defined force to cause controlled adjustment of the separation distance between the pin tips 41a, 42a. One skilled in the art will further recognize that the two-pin fluid handling system is not limited to a fulcrum for varying the separation distance and that any suitable mechanism for varying the separation distance may be utilized.

According to alternate embodiment, the one or both of the tip surfaces 70 and/or the outside shaft surface are coated with a hydrophilic, hydrophobic or other chemical coating to enhance droplet acquisition, handling and/or dispensing. For example, the tips 41, 42 may be formed of coated with a hydrophilic coating to enhance retention of a sample in the sample acquisition region. According to one embodiment, the outside shaft surfaces of the tips 41,42 are coated with gold or another suitable hydrophobic material without affecting the tip surfaces 70 defining the sample acquisition region 14. The use of a metal coating provides enhanced control over the volume and release of a droplet. The use of silicon and/or gold additionally allows for more vigorous cleaning solutions to be utilized when cleaning the tips without degrading the system. In this manner, contamination of the tips is reduced.

The coating may be applied in a pattern to the tip surfaces 70 or the other surfaces of the tips 41, 42 by shadow masking. The coating may be sputtered, or evaporated on a surface in a predetermined pattern, defined by a mask. One skilled in the art will recognize that any suitable pattern for directing the liquid sample and enhancing control over sample acquisition, handling and dispensing may be utilized.

According to another embodiment, the fluid handling system may comprise a single pin having a suitable pattern coating applied to the surfaces of the pin tip. For example, the shaft of the single pin may be coated with a suitable hydrophobic coating and the tip of the pin may be coated with a suitable hydrophilic coating to enhance acquisition, manipulation and dispensing of a liquid sample.

Figure 11:
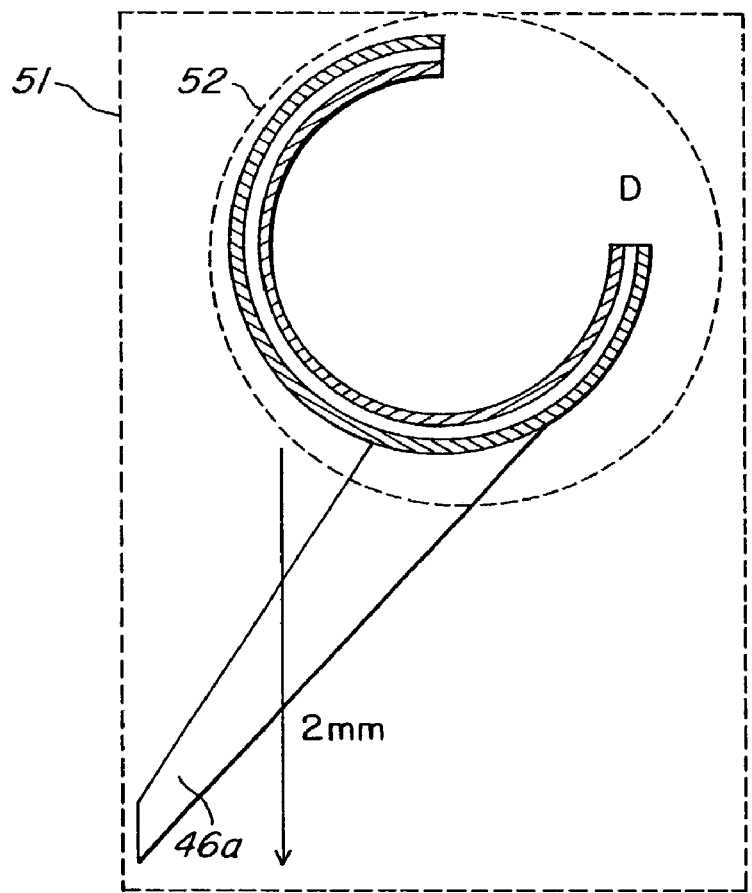
FIG. 11 is a detailed view of the relaxation region of the fluid handling system of FIG. 8.

FIG. 11 illustrates the relaxation region 51 of the fluid handling system 40 of FIG. 8. The relaxation region can comprise any suitable part, component or feature that allows the tip to handle or absorb a force applied thereto. The pin tips 41 and 42 may be brittle and subject to breakage when accidentally touched down to surfaces, due to their size and the material used to fabricate the pins. The illustrated relaxation region 51 comprises a spring 52 formed between the tip 41a and the substrate 43. When the tip 41a contacts a surface, the spring absorbs the impulse and retracts the tip 41a to prevent breakage. The springs 52 in the pins are configured to move the corresponding tip up and away from the other tip to prevent collision of the tips. The invention is not limited to the illustrative spring design. One skilled in the art will recognize that any suitable spring design may be utilized to form the relaxation region 51 to protect the pin tips from breakage.

According to an alternate embodiment, the spring 52 can optionally include one or more sensors to measure the force of contact between the tip and a surface. For example, differential piezoresistive sensors may be included in the spring 52 and connected to an actuator (not shown) to control the spring using feedback control loop. The spring sensor may also be utilized to measure the force exerted by the droplet on the tips, and allow the driver to compensate for variable forces exerted by the droplet on the tips.

According to an alternate embodiment of the present invention, a relaxation region may be implemented in a two-pin fluid handling system comprising a pair of spaced-apart, fixed pins defining a sample acquisition region of fixed volume.

As discussed, the fluid handling system 10 or 40 of the present invention may be microfabricated from a suitable substrate, such as silicon, glass or plastic. According to the illustrative embodiment, photolithography may be utilized to form the pin structures in the substrate. In photolithography, the pattern of the two pins and other components of the two-pin fluid handling system 10 or 40 are imprinted on a silicon wafer, or other substrate, using one or more photoresist layers that are patterned by UV or other light projected through one or more photo-masks containing the pattern on it. The substrate is then etched to fabricate the two-pin structure. One skilled in the art will recognize that any suitable microfabrication technique may be utilized to manufacture the two-pin fluid handling system of the illustrative embodiment of the present invention.

One skilled in the art will recognize that the described microfabrication technique may further be utilized to fabricate single-pin fluid handling systems from a silicon wafer or other suitable substrate. For example, it is within the scope of the invention to microfabricate a single-pin structure having two tips forming a sample channel for acquiring manipulating and dispensing a liquid sample, as described in U.S. Pat. No. 6,101,946, from a silicon wafer by etching the silicon wafer to define the pin and sample channel.

Figure 12:
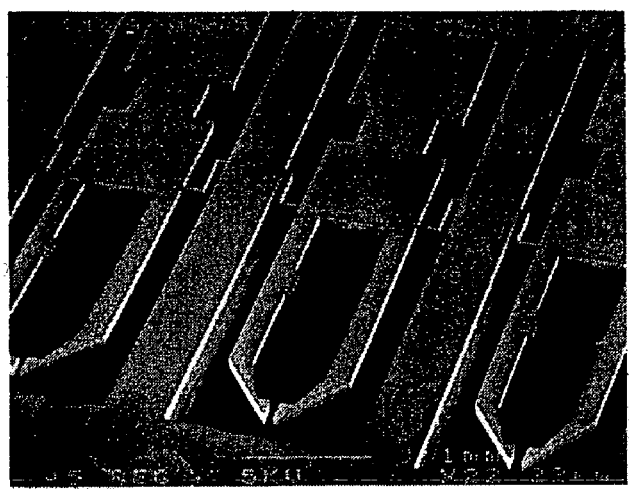
FIG. 12 is a scanning electron microscope (SEM) image of an array of pin assemblies that are microfabricated from a silicon wafer according to the teachings of the present invention.

FIG. 12 is a scanning electron microscope (SEM) image of an array of two-pin sample fluid handling systems 100 according to an embodiment of the invention and formed from a silicon wafer 101 using the above-described microfabrication technique. As shown, a plurality of two-pin fluid handling systems are fabricated from a single silicon wafer substrate. Each two-pin fluid handling system comprises a pair of elongated pins that are spaced apart to define a sample acquisition region between the tips of the pins.

Figure 13:
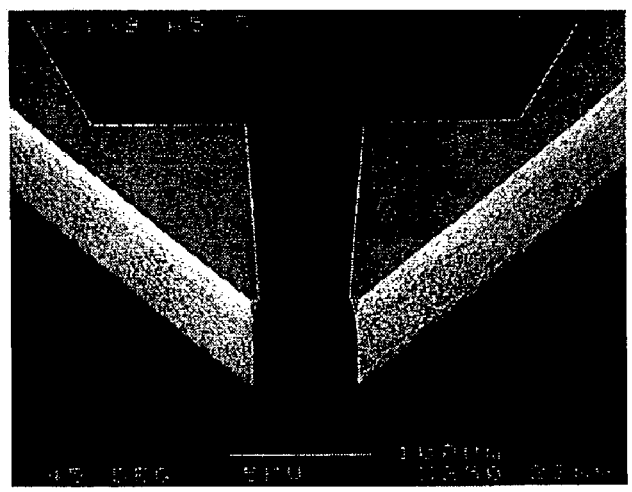
FIG. 13 is a SEM image showing a detailed view of a tip region of one of the fluid handling systems of FIG. 12.

FIG. 13 is another SEM image showing a detailed view of the tip region of one of the microfabricated two-pin fluid handling systems of FIG. 9. As shown, the pins are etched in a silicon wafer to define a sample acquisition region 140 between the tips of the pins. As illustrated, the microfabricated pin tips have a separation distance of less than about 100 microns.

Figure 14:
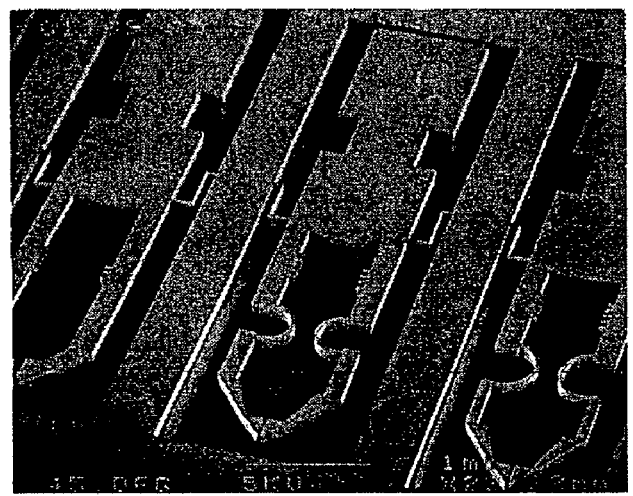
FIG. 14 is a SEM image illustrating an array of pin assemblies having relaxation regions that are microfabricated from a silicon wafer according to the teachings of the illustrative embodiment of the present invention.

FIG. 14 is another SEM image of an array of microfabricated two-pin sample fluid handling systems 110 having relaxation regions 51 according to an embodiment of the invention. As shown, the array is also formed from a silicon wafer 101 using the above-described microfabrication technique. The relaxation region 51 is formed by etching the silicon wafer in the region between the pin tips and the holder to define a spring for absorbing an impact on the tips. The relaxation region 51 prevents breakage of the pin tips 41, 42 when the pin tips contact a surface.

The fluid handling system of the present invention provides significant improvements to the process of forming, manipulating and dispensing droplets of samples for spotting and dilution applications. The illustrative configuration provides precise control over the amount of liquid sample that is acquired and deposited through the use of two pins having a variable separation distance. Adjusting the separation distance between the pin tips easily and precisely modifies the volume of the acquired liquid droplet and the deposited liquid droplet. Furthermore, measurements of the physical properties of the liquid volume can be made on the fly and the tip separation can be modified quickly and easily to compensate for variations. The use of sensors provides precise control of the tip separation distance to optimize the process of acquiring, manipulating and dispensing droplets of a liquid sample.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A fluid handling system, comprising:
   a pin assembly comprising a plurality of components formed on a single substrate for handling a fluid the plurality of components comprising a holder, a first pin extending from and integral with the holder, a second pin extending from and integral with the holder, the second pin spaced from the first pin to define a channel therebetween sized and dimensioned for receiving and retaining a fluid sample by capillary action; and
   a cooling element for cooling one of said components of the pin assembly, whereby a fluid to be handled by the pin assembly is cooled so as to reduce evaporation.

2. The fluid handling system of claim 1, wherein the cooling element is a Peltier element.

3. The fluid handling system of claim 1, wherein the cooling element reduces evaporation of the fluid volume held in the channel.

4. The fluid handling system of claim 1, wherein the pin assembly is formed according to a microfabrication technique.

5. The fluid handling system of claim 1, wherein the cooling element is attached to one of said components.

6. The fluid handling system of claim 1, wherein the cooling element cools the holder.

7. The fluid handling system of claim 1, further comprising a temperature control system including the cooling element for controlling the temperature of the pin assembly.

8. The fluid handling system of claim 7, wherein the temperature control system comprises:
   a temperature sensor for measuring an actual temperature of the fluid handling system; and
   a controller for comparing the actual temperature to a reference temperature and for actuating the cooling element to adjust the actual temperature to equal the reference temperature.

9. The fluid handling system of claim 8, wherein the temperature sensor comprises a thin-film resistor.

10. A liquid dispensing system for transferring liquids, comprising a pin-type liquid dispensing assembly including a cooled holder, a first pin extending from and integral with the holder, and a second pin extending from and integral with the holder, the second pin spaced from the first pin to define a channel therebetween sized and dimensioned for receiving and retaining a fluid sample by capillary action; and
   a cooling element for cooling the cooled holder, whereby a fluid to be handled by the pin pin-type liquid dispensing assembly is cooled so as to reduce evaporation.

11. The liquid dispensing system of claim 10, wherein the cooling element is a Peltier type element.

12. The liquid dispensing system of claim 10, wherein the pin-type liquid dispensing assembly is manufactured by microfabrication technology.

13. The liquid dispensing system of claim 10, further comprising a temperature control system for controlling the temperature of the liquid dispensing system.

14. The liquid dispensing system of claim 13, wherein the temperature control system comprises:
   a temperature sensor for measuring an actual temperature of the system; and
   a controller for comparing the actual temperature to a reference temperature and triggering the cooling element to adjust the actual temperature to equal the reference temperature.

15. The liquid dispensing system of claim 14, wherein the temperature sensor comprises a thin-film resistor.

16. The fluid handling system of claim 1, wherein the first pin and second pin are separated by a distance of less than about 100 microns where the channel is formed.

17. A method for reducing evaporation in a fluid handling system for handling a fluid, comprising the steps of:
   providing a pin assembly comprising a holder, first pin extending from and integral with the holder, a second pin extending from and integral with the holder, the second pin spaced from the first pin to define a channel sized and dimensioned for receiving and retaining a fluid by capillary action, wherein the holder, first pin and second pin are formed on a single substrate;
   receiving fluid through said channel;
   retaining said fluid in said channel; and
   lowering the temperature of one of first pin and the second pin to reduce evaporation of the fluid.

18. The method of claim 17, wherein the pin-type liquid dispensing assembly includes a cooling element and the step of lowering the temperature comprises activating the cooling element.

19. The method of claim 18, wherein the cooling element comprises a Peltier element.

20. The method of claim 17, further comprising the steps of:
   measuring the temperature of one of first pin and the second pin;
   comparing the measured temperature to a reference temperature; and
   modifying the temperature of one of first pin and the second pin if the measured temperature deviates from the reference temperature so that the measured temperature substantially matches the reference temperature.

21. A system for handling a liquid sample, comprising:
   a holder;
   a first pin coupled to the holder and having a first tip having a concavely curved surface;
   a second pin coupled to the holder and having a second tip with a concavely curved surface spaced a predetermined separation distance from the first tip to define a sample acquisition region between the concavely curved surfaces for holding the liquid sample; and
   a temperature control element for controlling the temperature of said first and second pin.

22. The fluid handling system of claim 21, wherein the predetermined separation distance between the two concave surfaces is less than about 100 microns.

23. The fluid handling system of claim 21, wherein each tip further comprises a body connecting the tips to the holder, and the body of the first pin is separated from the body of the second tip by a second distance that is larger than the predetermined separation stance between the first tip and second tip.

24. A fluid handling system, comprising
  a pin assembly for handling a fluid comprising a first pin that is stationary and a second pin that is movable, said pin assembly further comprising a fulcrum region for moving the movable second pin
  a temperature control element coupled to the pin assembly for controlling the temperature of the pin assembly, and
  a temperature sensor for sensing the temperature of the pin assembly, and a controller in circuit with the temperature control element and the temperature sensor for controlling the temperature of the pin assembly.

25. The fluid handling system of claim 24, wherein said pin assembly comprises a first pin having a tip, and a second pin having a tip, said tips of the first and second pins forming a region sized and configured for receiving the fluid.

26. The fluid handling system of claim 25, wherein said pin assembly further comprises a holder coupled to said first and second pins.

27. The fluid handling system of claim 25, wherein said pin assembly comprises a relaxation region located on one of said pins between a tip and a base of the pin.

28. The fluid handling system of claim 25, wherein said pin assembly further comprises an actuator for actuating at least one of said pins.

29. The fluid handling system of claim 28, wherein said pin assembly further comprises a sensor for sensing movement of one of said pins.

30. The fluid handling system of claim 24, further comprising a driver coupled to said fulcrum region for moving said second pin.

31. A pin assembly, comprising
  a first microfabricated pin formed on a silicon substrate,
  a second microfabricated pin formed on the silicon substrate, and
  a holder for holding the first and second pins formed on the silicon substrate; and
  a temperature control element coupled to one of said first pin, said second pin, and said holder for controlling the temperature of the pin assembly.

* * * * *